United States Patent
Hacker et al.

(10) Patent No.: US 6,919,299 B2
(45) Date of Patent: Jul. 19, 2005

(54) SYNERGISTIC HERBICIDAL COMPOSITIONS

(75) Inventors: Erwin Hacker, Hochheim (DE);
Hermann Bieringer, Eppstein (DE);
Hansjörg Krähmer, Hofheim (DE)

(73) Assignee: Bayer CropScience GmbH, Frankfurt (DE)

( * ) Notice: Subject to any disclaimer, the term of this patent is extended or adjusted under 35 U.S.C. 154(b) by 0 days.

(21) Appl. No.: 10/309,501

(22) Filed: Dec. 4, 2002

(65) Prior Publication Data

US 2003/0158040 A1 Aug. 21, 2003

(30) Foreign Application Priority Data

Dec. 7, 2001 (DE) .......................... 101 60 139

(51) Int. Cl.⁷ .................. A01N 37/34; A01N 35/06; A61K 31/33; A61K 31/12; A61K 31/21
(52) U.S. Cl. ................. 504/141; 504/118; 504/310; 504/348; 514/183; 514/506; 514/675
(58) Field of Search .................. 504/141, 118, 504/310, 348, 135, 136, 144; 514/183, 506, 675; 548/300.1, 316.4

(56) References Cited

U.S. PATENT DOCUMENTS

| | | | |
|---|---|---|---|
| 4,859,234 A | | 8/1989 | Alterman et al. |
| 5,385,881 A | * | 1/1995 | Schumacher et al. ........ 504/136 |
| 5,416,061 A | * | 5/1995 | Hewett et al. .............. 504/141 |
| 5,741,756 A | | 4/1998 | Shribbs |
| 5,801,121 A | * | 9/1998 | Kamano et al. ............. 504/288 |
| 5,922,646 A | * | 7/1999 | Schnabel et al. ............ 504/214 |
| 5,977,376 A | * | 11/1999 | Araki et al. ............. 548/268.6 |
| 5,981,432 A | | 11/1999 | Hudetz et al. |
| 6,048,984 A | * | 4/2000 | Araki et al. ............. 548/268.6 |
| 6,376,429 B1 | * | 4/2002 | Van Almsick et al. ...... 504/271 |
| 6,420,317 B1 | * | 7/2002 | Schmitt et al. ............. 504/282 |
| 6,498,126 B1 | * | 12/2002 | Hacker et al. .............. 504/134 |
| 6,576,593 B2 | * | 6/2003 | van Almsick et al. ...... 504/134 |
| 6,645,915 B1 | * | 11/2003 | Riebel et al. ............... 504/234 |
| 6,660,691 B2 | * | 12/2003 | Ziemer et al. .............. 504/106 |
| 6,703,348 B2 | * | 3/2004 | Almsick et al. ............ 504/271 |
| 6,770,594 B2 | * | 8/2004 | Bickers et al. .............. 504/212 |
| 6,774,086 B2 | * | 8/2004 | Seitz et al. ................. 504/224 |
| 6,809,064 B2 | * | 10/2004 | Auler et al. ................ 504/134 |
| 6,825,183 B2 | * | 11/2004 | Muller et al. ............... 514/183 |

FOREIGN PATENT DOCUMENTS

| | | |
|---|---|---|
| DE | 42 16 880 A1 | 11/1993 |
| EP | 0 230 596 B1 | 8/1987 |
| WO | WO-95/28839 | 11/1995 |
| WO | 95/29899 * | 11/1995 |
| WO | WO-97/48276 | 12/1997 |
| WO | 98/29406 * | 9/1998 |
| WO | WO 00/03592 | 1/2000 |
| WO | 00/21924 * | 4/2000 |
| WO | 01/28341 A3 * | 4/2001 |
| WO | WO 01/28341 A2 | 4/2001 |
| WO | 01/28341 A2 * | 4/2001 |
| WO | WO-01/43550 A2 | 6/2001 |
| WO | 01/74785 * | 10/2001 |

OTHER PUBLICATIONS

English Language Abstract of WO01/28341 (Apr. 26, 2001).*
European Patent Office; Patent Abstract of Japanese application No. 02414798 (Aug. 19, 1992); publication No. 04230301; Nippon Soda Co Ltd.
English language abstract: "Sulcotrione: a selective postemergence herbicide for corn;" Jean Marc Beraud, et al.; XP–002244610; (1993).
English language abstract of "New synergistic and selective herbicide compositions;" Kenneth Mason Publications; Hampshire, GB; XP–001087222; (2001).
English Language Abstract of DE–42 16 880–A1 (Nov. 25, 1993).

* cited by examiner

*Primary Examiner*—Sabiha N. Qazi
(74) *Attorney, Agent, or Firm*—Connolly Bove Lodge and Hutz LLP

(57) ABSTRACT

Herbicidal compositions comprising
  A) 2-[2-chloro-3-(2,2,2-trifluoroethoxymethyl)-4-methylsulfonyl-benzoyl]cyclohexane-1,3-dione and
  B) at least one compound from the group consisting of ethoxysulfuron, flumetsulam, halosulfuron, imazamox, imazapyr, imazaquin, imazethapyr, metosulam, nicosulfuron, primisulfuron, prosulfuron, rimsulfuron, thifensulfuron-methyl, triflusulfuron, foramsulfuron, ametryne, atrazine, bromoxynil, cyanazine, diuron, hexazinone, metribuzin, pyridate, terbuthylazine, 2,4-D, clopyralid, dicamba, diflufenzopyr, fluroxypyr, butylate, EPTC, fenoxaprop-P-ethyl, acetochlor, alachlor, dimethenamid, flufenacet, mefenacet, metolachlor, thenylchlor, S-metolachlor, fluthiacet-methyl, carfentrazone-ethyl, isoxaflutole, mesotrione, sulcotrione, 4-(4-trifluoromethyl-2-methylsulfonylbenzoyl)-5-hydroxy-1-methyl-3-methylpyrazole, glyphosate, pendimethalin, trifluralin, asulam, triaziflam, diflufenican and glufosinate-ammonium against monocotyledonous and/or dicotyledonous harmful plants are described.

The activity of these compositions is superior to that of the herbicides applied individually.

8 Claims, No Drawings

SYNERGISTIC HERBICIDAL COMPOSITIONS

The invention relates to the technical field of crop protection agents which can be used against unwanted vegetation and comprise, as active compounds, a combination of at least two herbicides.

More specifically, it relates to herbicidal compositions which comprise, as active compound, a herbicide from the group of the benzoylcyclohexanediones in combination with at least one further herbicide.

Herbicides of the abovementioned group of the benzoylcyclohexanediones are known from numerous documents. Thus, benzoylcyclohexandiones having herbicidal action are described, for example, in WO 98/29406 and WO 00/21924.

However, the use of the benzoylcyclohexanediones known from these applications frequently entails disadvantages in practice. Thus, the herbicidal activity of the known compounds is not always sufficient, or, if the herbicidal activity is sufficient, then undesired damage to the useful plants is observed.

The effectiveness of herbicides depends inter alia on the type of herbicide used, its application rate, the formulation, the harmful plants to be controlled in each case, climatic and soil conditions, etc. A further criterion is the persistency or the rate at which the herbicide is degraded. Changes in the susceptibility of harmful plants to an active compound which may occur on prolonged use or in specific geographical areas may also have to be taken into account. Such changes manifest themselves by a more or less pronounced loss in activity and can only be compensated to a limited extent by higher herbicide application rates.

Owing to the large number of possible influencing factors, there is virtually no individual active compound which has all the desired properties for different requirements, in particular with respect to the species of harmful plants and the climatic zones. Furthermore, there is the permanent objective to achieve the desired effect using more and more reduced herbicide application rates. A lower application rate reduces not only the amount of active compound required for the application, but generally also reduces the amount of formulation auxiliaries required. Both reduce the economic expense and improve ecological compatibility of the herbicide treatment.

A frequently used method for improving the use profile of a herbicide is the combination of the active compound with one or more other active compounds which contribute the desired additional properties. However, when two or more active compounds are applied in combination, it is not uncommon for phenomena of physical and biological incompatibility to occur, for example insufficient stability of a joint formulation, decomposition of an active compound or antagonism of the active compounds. What is desired are, in contrast, active compound combinations having a favorable activity profile, high stability and, if possible, synergistically enhanced activity, thus permitting the application rate to be reduced, compared with the individual application of the active compounds to be combined.

WO 01/28341 discloses combinations of herbicides from the group of the inhibitors of hydroxyphenylpyruvate dioxygenase and numerous other herbicides of other substance and activity classes. However, the combinations disclosed therein do not always meet the required criteria with respect to a favorable activity profile, high stability and, if possible, synergistically enhanced activity.

It is an object of the present invention to provide herbicidal compositions having better properties than those of the prior art.

The invention provides herbicidal compositions, comprising an effective amount of A) the compound 2-[2-chloro-3-(2,2,2-trifluoroethoxymethyl)-4-methylsulfonylbenzoyl]cyclohexane-1,3-dione or an agriculturally suitable salt thereof (component A)

and

B) at least one compound (component B) from one of the following groups

B1 inhibitors of the biosynthesis of branched amino acids: ethoxysulfuron (B1.1), flumetsulam (B1.2), halosulfuron (B1.3), imazamox (B1.4), imazapyr (B1.5), imazaquin (B1.6), imazethapyr (B1.7), metosulam (B1.8), nicosulfuron (B1.9), primisulfuron (B1.10), prosulfuron (B1.11), rimsulfuron (B1.12), thifensulfuron-methyl (B1.13), triflusulfuron (B1.14), N-[(4,6-dimethoxypyrimidin-2-yl)aminocarbonyl]-2-dimethylaminocarbonyl-5-formylaminobenzenesulfonamide (foramsulfuron) (B1.15);

B2 inhibitors of the photosynthesis electron transport: ametryne (B2.1), atrazine (B2.2), bromoxynil (B2.3), cyanazine (B2.4), diuron (B2.5), hexazinone (B2.6), metribuzin (B2.7), pyridate (B2.8), terbuthylazine (B2.9);

B3 synthetic auxins: 2,4-D (B3.1), clopyralid (B3.2), dicamba (B3.3), diflufenzopyr (B3.4), fluroxypyr (B3.5), B4 inhibitors of fatty acid biosynthesis: butylate (B4.1), EPTC (B4.2), fenoxaprop-P-ethyl (B4.3);

B5 inhibitors of cell division: acetochlor (B5.1), alachlor (B5.2), dimethenamid (B5.3), flufenacet (B5.4), mefenacet (B5.5), metolachlor (B5.6), S-metolachlor (B5.7), thenylchlor (B5.8);

B6 inhibitors of protoporphyrinogen oxidase fluthiacetmethyl (B6.1), carfentrazone-ethyl (6.2);

B7 inhibitors of hydroxyphenylpyruvate dioxygenase isoxaflutole (B7.1), mesotrione (B7.2), sulcotrione (B7.3), 4-(4-trifluoromethyl-2-methylsulfonylbenzoyl)-5-hydroxy-1-methyl-3-methylpyrazole (B7.4);

B8 glyphosate (B8.1);
B9 pendimethalin (B9.1);
B10 trifluralin (B10.1);
B11 asulam (B11.1);
B12 triaziflam (B12.1);
B13 diflufenican (B13.1) and
B14 glufosinate-ammonium (B14.1), where this composition comprises the component A or a salt thereof and the compounds of group B1 to B14 (component B) in a weight ratio of from 1:2000 to 2000:1.

2-[2-Chloro-3-(2,2,2-trifluoroethoxymethyl)-4-methylsulfonylbenzoyl]cyclohexane-1,3-dione (component A) is known from WO 00/21924. N-[(4,6-Dimethoxypyrimidin-2-yl)aminocarbonyl]-2-dimethylaminocarbonyl-5-formylaminobenzenesulfonamide is known from WO 95/29899. 4-(4-Trifluoromethyl-2-methylsulfonylbenzoyl)-5-hydroxy-1-methyl-3-methylpyrazole is known from WO 01/74785; cf. the table. The other herbicides referred to by their common names are known, for example, from "The Pesticide Manual", 12th edition, 2000, British Crop Protection Council.

TABLE

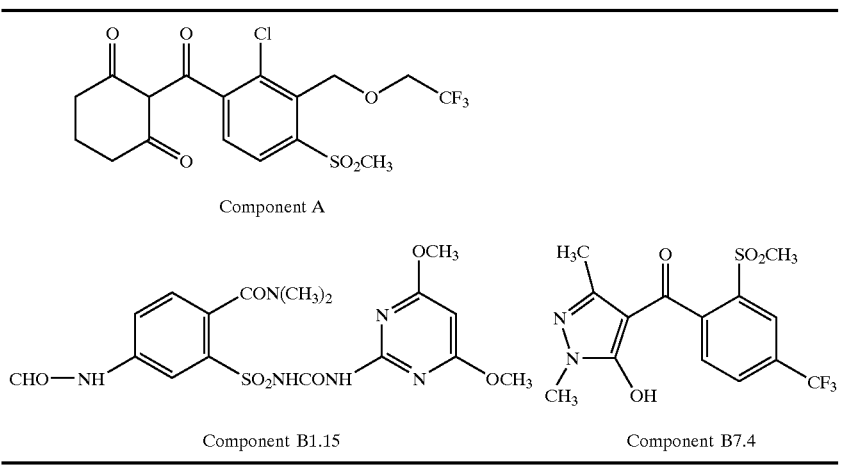

The three publications quoted above contain detailed statements about preparation processes and starting materials. The disclosure of these publications is expressly incorporated into this description by way of reference.

In the combinations according to the invention, application rates in the range from 1 to 2000 g, preferably from 10 to 500 g, of active ingredient per hectare (ai/ha) of component A and from 1 to 2000 g, preferably from 1 to 500 g, of component B are generally required.

The weight ratios of the components A to B to be used can be varied within wide ranges. The ratio is preferably in the range from 1:50 to 500:1, in particular in the range from 1:20 to 50:1. Optimum weight ratios may depend on the particular field of application, on the weed spectrum and the active compound combination used and can be determined in preliminary experiments.

The compositions according to the invention can be employed for the selective control of annual and perennial monocotyledonous and dicotyledonous harmful plants in crops of cereals (for example barley, oats, rye, wheat), corn and rice crops and in crops of transgenic useful plants or crops of useful plants selected by classical means which are resistant to active compounds A and B. Likewise, they can be employed for controlling undesirable harmful plants in plantation crops such as oil palm, coconut palm, Indian-rubber tree, citrus, pineapple, cotton, coffee, cocoa, sugarcane and the like, and also in fruit production and viticulture. They are particularly suitable for controlling monocotyledonous and/or dicotyledonous harmful plants in corn and sugarcane.

The compositions according to the invention act against a broad spectrum of weeds. They are suitable, for example, for controlling annual and perennial harmful plants such as, for example, from the species Abutilon, Alopecurus, Avena, Chenopodium, Cynoden, Cyperus, Digitaria, Echinochloa, Elymus, Galium, Ipomoea, Lamium, Matricaria, Scirpus, Setaria, Sorghum, Veronica, Viola and Xanthium.

The herbicidal compositions according to the invention are also distinguished by the fact that the effective dosages of components A and B used in the combinations are reduced with respect to an individual dosage, so that it is possible to reduce the required active compound application rates.

Thus, the combinations mentioned below are combinations according to the invention:
(A+B1.1), (A+B1.2), (A+B1.3), (A+B1.4), (A+B1.5), (A+B1.6), (A+B1.7), (A+B1.8), (A+B1.9), (A+B1.10), (A+B1.11), (A+B1.12), (A+B1.13), (A+B1.14), (A+B1.15);
(A+B2.1), (A+B2.2), (A+B2.3), (A+B2.4), (A+B2.5), (A+B2.6), (A+B2.7), (A+B2.8), (A+B2.9);
(A+B3.1), (A+B3.2), (A+B3.3), (A+B3.4), (A+B3.5);
(A+B4.1), (A+B4.2), (A+B4.3);
(A+B5.1), (A+B5.2), (A+B5.3), (A+B5.4), (A+B5.5), (A+B5.6), (A+B5.7), (A+B5.8);
(A+B6.1), (A+B6.2); (A+B7.1), (A+B7.2), (A+B7.3), (A+B7.4);
(A+B8.1); (A+B9.1); (A+B10.1); (A+B11.1); (A+B12.1); (A+B13.1) and (A+B14.1).

Preference is given to the combinations (A+B1.1), (A+B1.8), (A+B1.9), (A+B1.10), (A+B1.11), (A+B1.12), (A+B1.15).

Preference is also given to the combinations (A+B2.2), (A+B2.3), (A+B2.7).

Preference is also given to the combinations (A+B3.1), (A+B3.2), (A+B3.3).

Preference is also given to the combinations (A+B5.1), (A+B5.3), (A+B5.4), (A+B5.6), (A+B5.7).

Preference is also given to the combination (A+B7.1).
Preference is also given to the combination (A+B8.1).
Preference is also given to the combination (A+B9.1).
Preference is also given to the combination (A+B14.1).

In addition, advantageous effects can be obtained using combinations comprising component A and two different components B.

The invention also provides a method for controlling unwanted vegetation, which comprises applying one or more herbicides A and one or more herbicides B to the harmful plants, to parts of the harmful plants or to the area under cultivation.

When herbicides of type A and B are applied jointly, superadditive (=synergistic) effects are observed. The activity in the combinations is more pronounced than the expected sum of the activities of the individual herbicides employed and the activity of the particular individual herbicide A and B. The synergistic effects permit the application rate to be reduced, a broader spectrum of broad-leaved weeds and weed grasses to be controlled, more rapid onset of the herbicidal action, a more prolonged action, better control of the harmful plants with only one application, or few applications, and widening of the period of time within which the product can be used. These properties are required in weed control practice to keep agricultural crops free from undesirable competing plants and thus to ensure and/or to increase quality and quantity of the yields. These novel combinations markedly surpass the prior art with respect to the described properties.

The active compound combinations according to the invention can either be present as mixed formulations of the components A and B, if appropriate together with other customary formulation auxiliaries, which mixed formulations are then applied in the usual manner in the form of a dilution with water, or else they can be prepared in the form of so-called tank mixes by joint dilution with water of the components which are formulated separately, or partly separately.

The components A and B can be formulated in various ways, depending on the prevailing biological and/or physicochemical parameters. Suitable general possibilities for formulations are, for example: wettable powders (WP), emulsifiable concentrates (EC), aqueous solutions (SL), emulsions (EW) such as oil-in-water and water-in-oil emulsions, sprayable solutions or emulsions, oil- or water-based dispersions, suspoemulsions, dusts (DP), seed dressing products, granules for soil application or for broadcasting or water-dispersible granules (WG), ULV formulations, microcapsules or waxes.

The individual types of formulation are known in principle and are described, for example, in: Winnacker-Küchler, "Chemische Technologie" [Chemical Technology], Vol. 7, C. Hauser Verlag Munich, 4th Ed. 1986; van Valkenburg, "Pesticides Formulations", Marcel Dekker N.Y., 1973; K. Martens, "Spray Drying Handbook", 3rd Ed. 1979, G. Goodwin Ltd. London. The formulation auxiliaries required, such as inert materials, surfactants, solvents and other additives, are also known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry"; 2nd Ed., J. Wiley & Sons, N.Y.; Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesellschaft, Stuttgart 1976; Winnacker-Küchler, "Chemische Technologie" [Chemical Technology], Vol. 7, C. Hauser Verlag Munich, 4th Ed. 1986.

Based on these formulations, it is also possible to prepare combinations with other pesticidally active substances, such as other herbicides, fungicides or insecticides, and also safeners, fertilizers and/or growth regulators, for example in the form of a ready mix or tank mix.

On application, the combinations according to the invention of components A and B frequently only cause little damage, if any, to useful plants. To reduce damage to useful plants to an acceptable minimum, or to eliminate damage to useful plants completely, it is also possible, in a further preferred embodiment, to apply the combinations according to the invention of components A and B as a mixture with a safener of the formula (I) or (II)

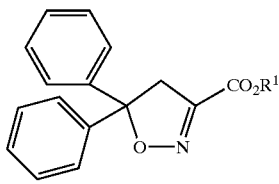

(I)

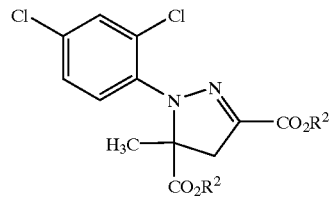

(II)

where $R^1$ is hydrogen, methyl or ethyl and $R^2$ is methyl or ethyl. The compounds of the formula (I) are known from WO 95/07897 and the literature cited therein and can be prepared according to or analogously to the processes described therein. The compounds of the formula (II) are known from EP-A 0 635 996 and the literature cited therein and can be prepared according to or analogously to the processes described therein. The two publications cited contain detailed statements about preparation processes and starting materials. These publications are expressly incorporated into this description by way of reference.

Wettable powders are preparations which are uniformly dispersible in water and which, besides the active compound, also comprise ionic or nonionic surfactants (wetting agents, dispersants), for example polyethoxylated alkylphenols, polyethoxylated fatty alcohols or fatty amines, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or an inert substance.

Emulsifiable concentrates are prepared by dissolving the active compound in an organic solvent, for example butanol, cyclohexanone, dimethylformamide, xylene or else higher-boiling aromatics or hydrocarbons, with the addition of one or more ionic or nonionic surfactants (emulsifiers). Examples of emulsifiers which can be used are: calcium alkylarylsulfonates, such as calcium dodecylbenzenesulfonate, or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxyethylene sorbitol esters.

Dusts are obtained by grinding the active compound with finely divided solid materials, for example talc, natural clays, such as kaolin, bentonite and pyrophyllite, or diatomaceous earth.

Granules can be prepared either by spraying the active compound onto adsorptive, granulated inert material, or by applying active compound concentrates to the surface of carriers, such as sand, kaolinite or granulated inert material, with the aid of binders, for example polyvinyl alcohol, sodium polyacrylate or else mineral oils. Suitable active compounds can also be granulated in the manner customary for the preparation of fertilizer granules, if desired as a mixture with fertilizers. Water-dispersible granules are, in general, prepared by processes such as spray-drying, fluidized-bed granulation, disk granulation, mixing using high-speed mixers, and extrusion without solid inert material.

The agrochemical preparations generally comprise from 0.1 to 99 percent by weight, in particular from 0.2 to 95% by weight, of active compounds of types A and B, the following concentrations being customary, depending on the type of formulation: In wettable powders, the active compound concentration is, for example, approximately 10 to 95% by weight, the remainder to 100% by weight being composed of customary formulation components. In the case of emulsifiable concentrates, the active compound concentration can be, for example, from 5 to 80% by weight. Formulations in the form of dusts in most cases comprise from 5 to 20% by weight of active compound, sprayable solutions approximately 0.2 to 25% by weight of active compound. In the case of granules, such as dispersible granules, the active compound content depends partly on whether the active compound is in liquid or solid form and on which granulation auxiliaries and fillers are used. In general, the content in the water-dispersible granules amounts to between 10 and 90% by weight. In addition, the active compound formulations mentioned comprise, if appropriate, the tackifiers, wetting agents, dispersants, emulsifiers, preservatives, antifreeze agents, solvents, fillers, colorants, carriers, antifoams, evaporation inhibitors and pH or viscosity regulators which are customary in each case.

For use, the formulations, which are in commercially available form, are, if appropriate, diluted in a customary manner, for example using water in the case of wettable powders, emulsifiable concentrates, dispersions and water-dispersible granules. Preparations in the form of dusts, soil granules, granules for spreading and sprayable solutions, are conventionally not diluted any further with other inert substances prior to use.

The active compounds can be applied to the plants, parts of the plants, seeds of the plants or the area under cultivation (tilled soil), preferably to the green plants and parts of the plants and, if desired, additionally to the tilled soil.

A possible use is the joint application of the active compounds in the form of tank mixes, where the concentrated formulations of the individual active substances, in the form of their optimal formulations, are mixed jointly with water in the tank, and the spray mixture obtained is applied.

A joint herbicidal formulation of the combination according to the invention of the components A and B has the advantage that it can be applied more easily because the amounts of the components have already been adjusted with respect to one another to the correct ratio. Moreover, the auxiliaries of the formulation can be selected to suit each other in the best possible way, while a tank mix of various formulations may result in undesirable combinations of auxiliaries.

A. FORMULATION EXAMPLES a) A dust (WP) is obtained by mixing 10 parts by weight of an active compound/active compound mixture and 90 parts by weight of talc as inert substance and comminuting the mixture in a hammer mill.

b) A wettable powder (WG) which is readily dispersible in water is obtained by mixing 25 parts by weight of an active compound/active compound mixture, 64 parts by weight of kaolin-containing quartz as inert substance, 10 parts by weight of potassium lignosulfonate and 1 part by weight of sodium oleoylmethyltaurinate as wetting agent and dispersant, and grinding the mixture in a pinned-disk mill.

c) A dispersion concentrate which is readily dispersible in water is obtained by mixing 20 parts by weight of an active compound/active compound mixture with 6 parts by weight of alkylphenol polyglycol ether (Triton X 207), 3 parts by weight of isotridecanol polyglycol ether (8 EO) and 71 parts by weight of paraffinic mineral oil (boiling range for example approximately 255 to 277° C.) and grinding the mixture in a ball mill to a fineness of below 5 microns.

d) An emulsifiable concentrate (EC) is obtained from 15 parts by weight of an active compound/active compound mixture, 75 parts by weight of cyclohexanone as solvent and 10 parts by weight of ethoxylated nonylphenol as emulsifier.

e) Water-dispersible granules are obtained by mixing 75 parts by weight of an active compound/active compound mixture,
10 parts by weight of calcium lignosulfonate,
5 parts by weight of sodium lauryl sulfate,
3 parts by weight of polyvinyl alcohol and
7 parts by weight of kaolin
grinding the mixture in a pinned-disk mill and granulating the powder in a fluidized bed by spraying on water as granulation liquid.

f) Water-dispersible granules are also obtained by homogenizing and precomminuting, in a colloid mill,
25 parts by weight of an active compound/active compound mixture,
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water,
subsequently grinding the mixture in a bead mill and atomizing and drying the resulting suspension in a spray tower by means of a single-substance nozzle.

B. BIOLOGICAL EXAMPLES

Outdoors, crop plants were grown on plots of a size of from 5 to 10 m$^2$ on various soils and under various climatic conditions, and the natural presence of harmful plants and/or their seeds in the soil was utilized for the experiments. The treatment with the compositions according to the invention or the herbicides A and B applied individually was carried out after emergence of the harmful and the crop plants, in general at the 2- to 4-leaf stage. The active compounds or active compound combinations, formulated as WG, WP or EC, were applied by the post-emergence method. After 2 to 8 weeks, visual evaluation was carried out in comparison with an untreated comparative group. It was found that the compositions according to the invention have synergistic herbicidal action against economically important mono- and dicotyledonous harmful plants, i.e. that most of the compositions according to the invention have higher, some considerably higher, herbicidal activity than the sum of the activities of the individual herbicides. In addition, the herbicidal activities of the compositions according to the invention exceed the expected values according to Colby. In contrast, the treatment caused insignificant, if any, damage to the crop plants.

If the observed activity values of the mixtures already exceed the formal sum of the values for the trials with individual applications, they also exceed the expected value according to Colby which is calculated using the following formula (cf. S. R. Colby; in Weeds 15 (1967) pp. 20 to 22):

$$E = A + B - (A \times B / 100)$$

The figures denote:

A, B=Activity of components A and B in percent, at a dosage of a and b gram of ai/ha, respectively.

E=Expected value in % at a dosage of a+b gram of ai/ha.

The values observed in the experimental examples below exceed the expected values according to Colby.

The abbreviations denote:

| | | | |
|---|---|---|---|
| ABUTH | *Abutilon theophrasti* | BRAPP | *Brassica napus* |
| ECHCG | *Echinocloa crus galli* | GALAP | *Galium aparine* |
| MATCH | *Matricaria spec* | PAPRH | *Papaver rhoeas* |
| POLCO | *Polygonum convolvulus* | SETFA | *Setaria faberi* |
| AMARE | *Amaranthus retroflexus* | DIGSA | *Digitaria sanguinalis* |
| POROL | *Portulaca oleracea* | SORHA | *Sorghum halepense* |

The following compounds were used in the examples:

| Component | |
|---|---|
| A | 2-[2-Chloro-3-(2,2,2-trifluoroethoxymethyl)-4-methylsulfonyl-benzoyl]cyclohexane-1,3-dione |
| B2.2 | atrazine |
| B2.3 | bromoxynil |
| B1.9 | nicosulfuron |

Example B.I

| | | GALAP | | PAPRH | |
|---|---|---|---|---|---|
| Compound | Dosage [g ai/ha] | found | Value E, according to Colby | found | Value E, according to Colby |
| A | 75 | 50% | | 0% | |
| B2.2 | 200 | 30% | | 60% | |
| A + B2.2 | 75 + 200 | 90% | 68% | 75% | 60% |

Example B.II

| | | BRAPP | | SETFA | |
|---|---|---|---|---|---|
| Compound | Dosage [g ai/ha] | found | Value E, according to Colby | found | Value E, according to Colby |
| A | 100 | 68% | | 65% | |
| B2.2 | 840 | 0% | | 5% | |
| A + B2.2 | 100 + 840 | 80% | 68% | 83% | 67% |

Example B.III

| | | ABUTH | | ECHCG | |
|---|---|---|---|---|---|
| Compound | Dosage [g ai/ha] | found | Value E, according to Colby | found | Value E, according to Colby |
| A | 100 | 75% | | 98% | |
| B2.2 | 840 | 20% | | 0% | |
| A + B2.2 | 100 + 840 | 95% | 80% | 100% | 98% |

Example B.IV

| | | ABUTH | | ECHCG | |
|---|---|---|---|---|---|
| Compound | Dosage [g ai/ha] | found | Value E, according to Colby | found | Value E, according to Colby |
| A | 100 | 75% | | 98% | |
| B2.2 | 840 | 20% | | 0% | |
| A + B2.2 | 100 + 840 | 95% | 80% | 100% | 98% |

Example B.V

| | | MATCH | | POLCO | |
|---|---|---|---|---|---|
| Compound | Dosage [g ai/ha] | found | Value E, according to Colby | found | Value E, according to Colby |
| A | 38 | 45% | | 50% | |
| B2.3 | 100 | 55% | | 45% | |
| A + B2.3 | 38 + 100 | 97% | 75% | 80% | 73% |

Example B.VI

| | | AMARE | | POROL | |
|---|---|---|---|---|---|
| Compound | Dosage [g ai/ha] | found | Value E, according to Colby | found | Value E, according to Colby |
| A | 75 | 90% | | 50% | |
| B1.9 | 40 | 90% | | 0% | |
| A + B1.9 | 75 + 40 | 100% | 99% | 70% | 50% |

Example B.VII

| | | DIGSA | | SORHA | |
|---|---|---|---|---|---|
| Compound | Dosage [g ai/ha] | found | Value E, according to Colby | found | Value E, according to Colby |
| A | 75 | 46% | | 50% | |
| B1.9 | 40 | 50% | | 62% | |
| A + B1.9 | 75 + 40 | 81% | 73% | 95% | 79% |

What is claimed is:

1. A herbicidal composition, comprising a synergistically effective amount of

A) the compound 2-[2-chloro-3-(2,2,2-trifluoroethoxymethyl)-4-methylsulfonyl-benzoyl]

cyclohexane-1,3-dione or an agriculturally suitable salt thereof (component A)
and B) at least one compound (component B) selected from the group consisting of nicosulfuron, atrazine and bromoxynil.

2. The herbicidal composition as claimed in claim 1, which comprises, as component B, nicosulfuron.

3. The herbicidal composition as claimed in claim 1, which comprises, as component B, atrazine.

4. The herbicidal composition as claimed in claim 1 wherein the weight ratio A:B of components A and B is in the range from 1:20 to 50:1.

5. The herbicidal composition as claimed in claim 1 which comprises 0.1–99% by weight of components A and B and 99 to 0.1% by weight of formulating agents customary in crop protection.

6. The herbicidal composition as claimed in claim 1 which comprises a compound of the formula (I) or (II)

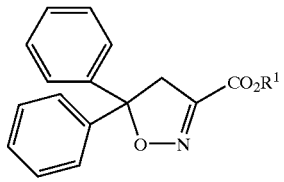
(I)

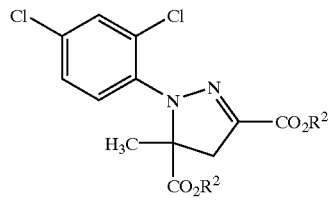
(II)

where $R^1$ is hydrogen, methyl or ethyl and $R^2$ is methyl or ethyl.

7. A method for controlling unwanted vegetation, which comprises applying component A and one or more components B to the harmful plants, to parts of harmful plants or to the area under cultivation, the combination of components A and B being as defined in claim 1.

8. A method for controlling unwanted vegetation comprising applying to the harmful plants the combination of components A and B as defined in claim 1.

* * * * *